United States Patent [19]

Friedman

[11] Patent Number: 4,661,070
[45] Date of Patent: Apr. 28, 1987

[54] METHOD FOR BLEACHING DISCOLORED TEETH

[76] Inventor: Joshua Friedman, 13 Fairfield Ct., Ridgefield, Conn. 06877

[21] Appl. No.: 840,194

[22] Filed: Mar. 17, 1986

[51] Int. Cl.4 ............................................. A61C 13/08
[52] U.S. Cl. ................................. 433/203.1; 433/215; 433/229
[58] Field of Search ........................ 433/215, 203, 229

[56] References Cited

U.S. PATENT DOCUMENTS 4,445,858  5/1984  Johnson .............................. 433/229
4,615,679 10/1986  Wyztt ................................. 433/229

Primary Examiner—Robert Peshock
Attorney, Agent, or Firm—E. Lieberstein

[57] ABSTRACT

A method for bleaching stained teeth by applying a concentrated solution of peroxide to the stained teeth and focusing a beam of light at the teeth with the beam containing the combination of ultraviolet and infrared energy for activating the peroxide solution.

6 Claims, 6 Drawing Figures

METHOD FOR BLEACHING DISCOLORED TEETH

FIELD OF INVENTION

This invention relates to an improved dental method for bleaching non-vital and vital teeth.

BACKGROUND OF INVENTION

Discoloration in non-vital teeth is often a consequence of endodontic root canal treatment and is also observed in traumatized teeth causing a loss of pulpal vitality. Root canal therapy may cause the treated teeth to darken with time and appear grey in contrast to the normally lighter adjacent dentition. Vital teeth may become stained due to tetracycline prescribed for the mother in her third trimester of pregnancy. As a result such patients may develop a brown or yellow mottled stained appearance in the anterior incisors. Other sources of stains in teeth may come from drinking water with a high content of minerals such as fluoride or iron. These intrinsic stains are not able to be removed by conventional prophylaxis treatments.

One method for treating the discoloration of teeth is bleaching. Bleaching is currently practiced by applying a concentrated hydrogen peroxide solution to the stained tooth and heating the tooth so treated with a bleaching instrument such as an electrically heated metal tip. A bleaching agent of concentrated peroxide solution such as "superoxol" is commercially available for this purpose. Superoxol is a 30 percent solution by weight of hydrogen peroxide in distilled water. The heated metal tip operates much like a soldering iron to raise the tooth to a temperature in the neighborhood of 120 to 140 degrees F. This temperature activates the peroxide solution accelerating the generation of free radicals which enhances the bleaching effect.

Alternatively, a high intensity lamp providing infrared heating energy is used also at approximately 12 inches from the patient's face to heat the area where the tooth is being treated for bleaching.

Existing methods of bleaching have many limitations. The metal tip of the bleaching unit contacts the tooth poorly and does not provide uniform heating of the tooth. There is also an inherent danger of burning adjacent soft tissues and electrical shock. The bleaching lamp produces heat that is so intense that substantial danger exists to the soft tissue which may suffer burns and/or discomfort. Injuries to the adjacent teeth may also occur, due to the large area of radiation.

SUMMARY OF INVENTION

The method of the present invention simultaneously applies both infrared and ultraviolet energy in combination and in a predetermined balance to activate the peroxide bleaching solution with substantially less energy than is required using heat energy alone. The source of combined infrared and ultraviolet energy is directed to the tooth being treated by a light guide which distributes light evenly across the tooth surface and applies this energy only to the tooth being treated. The tooth surface is heated evenly and activates the peroxide solution to cause uniform bleaching. Moreover, it poses no danger of adjacent teeth or tissues. The combination of infrared and ultraviolet energy has a synergistic effect on the efficiency of bleaching at a level lower than that provided by the application of infrared or ultraviolet energy alone. Accordingly, much less heat is required with the present invention to achieve the same bleaching effect.

The method of the present invention for treating discolored teeth comprises:
- applying a concentrated solution of peroxide to the pulp chamber of non-vital teeth and/or to the discolored surfaces of the non-vital teeth and vital teeth to be treated respectively;
- focusing a beam of optical energy directly upon each tooth to be treated containing ultraviolet energy in the 320 to 420 nanometer range in combination with infrared energy in the 700 to 1200 nanometer range for activating said peroxide solution; and
- substantially suppressing and blocking energy in the 500 to 700 nanometer range from reaching the tooth to be treated.

BRIEF DESCRIPTION OF THE DRAWINGS

Other advantages, objects and features of the present invention are apparent in the detailed description of the invention when read in conjunction with the accompanying drawings of which.

DETAILED DESCRIPTION OF THE INVENTION

Figure 1:
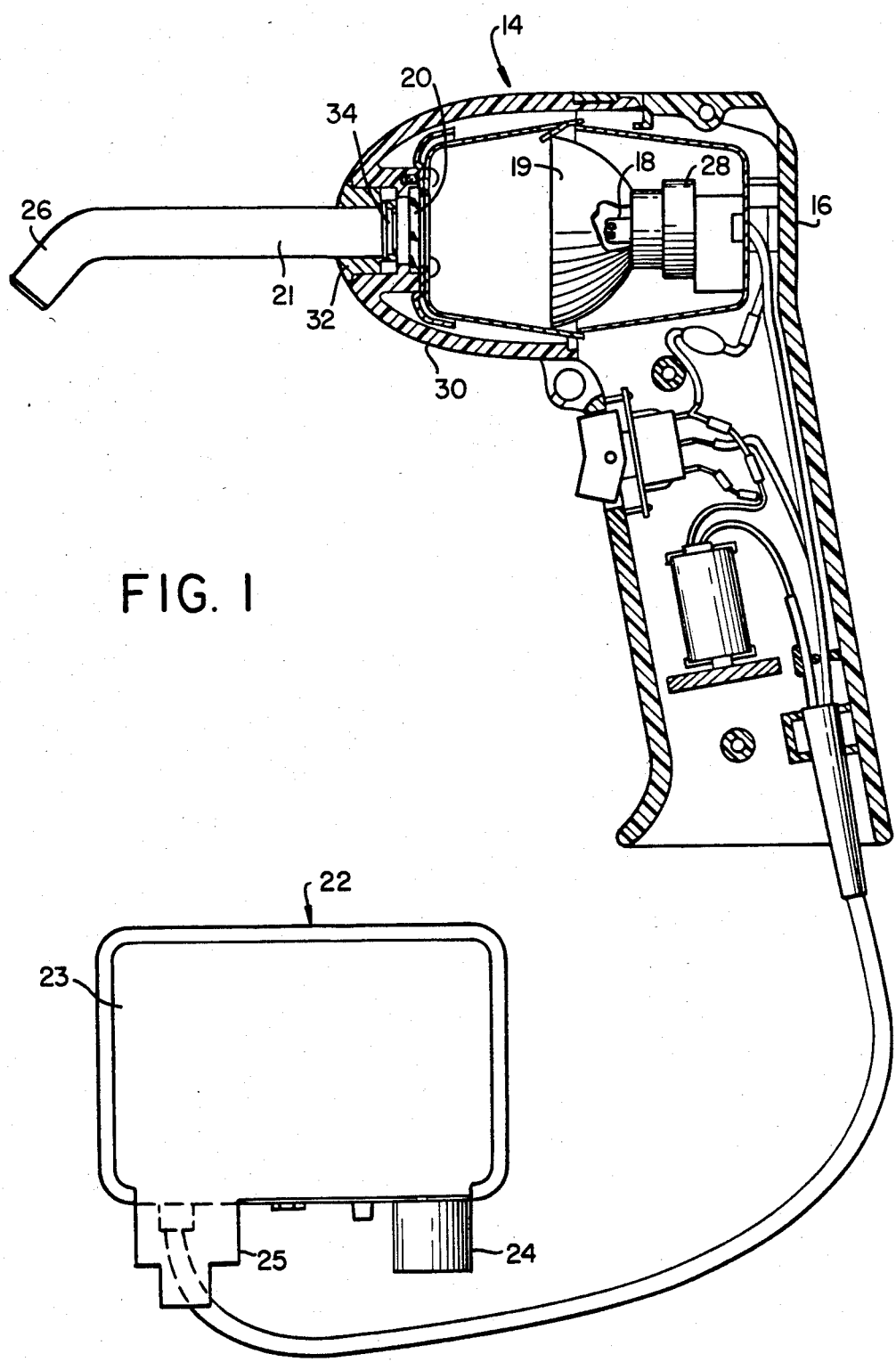
FIG. 1 is a longitudinal sectional view of a hand held light transmitting device for generating radiant energy in accordance with the present invention.
Figure 2:
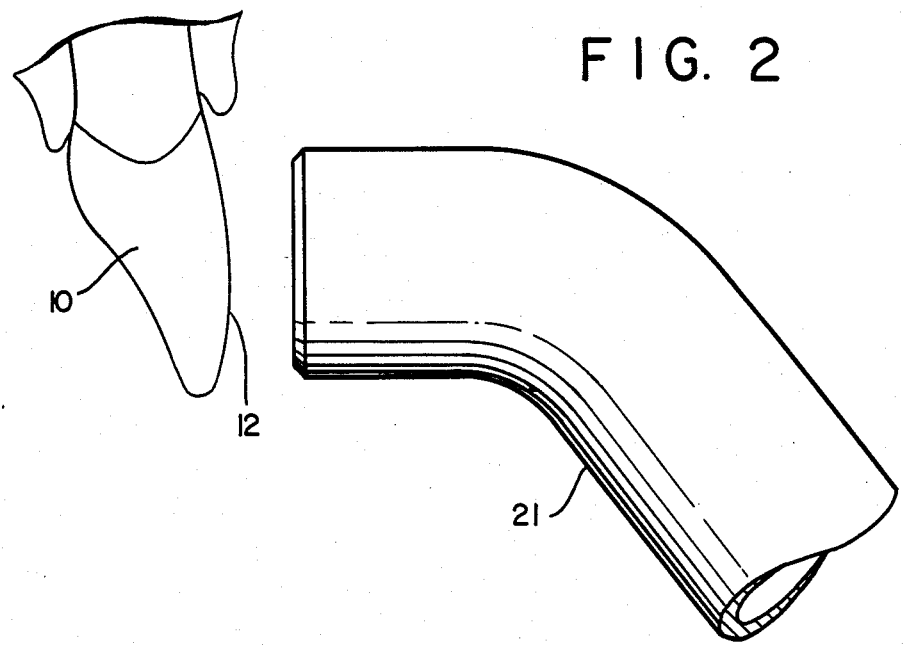
FIG. 2 is a diagrammatic illustration of an anterior tooth being treated with radiant energy in accordance with the present invention.

Bleaching is used for treating teeth which have been discolored by endodontic trreatment, tetracycline or high mineral content in the drinking water. Once the tooth is discolored, a procedure known to remove the discoloration is bleaching of the tooth. Preparation for bleaching involves applying a concentrated solution of hydrogen peroxide to the tooth. Referring to FIGS. 1–4 in general and to FIG. 2 in particular, the exposed labial surface 12 of an anterior tooth 10 is then irradiated with radiant energy from the light transmitting device 14 of FIG. 1 through the optic light guide 21. The optic light guide 21 may be held close to the tooth surface preferably only 1–3 mm away. The light guide 21 may actually be held against the tooth surface although this is less preferred.

The light transmitting device 14 represents an assembly comprising a housing 16 containing a source of radiant energy such as a halogen lamp 18, a reflector 19 for the lamp 18, an optical filter element 20, a fiber optic light guide 21 and a remote control unit 22. The remote control unit 22 includes a conventional power supply 23, a rheostat or other variable resistor 24 for adjusting the light in density and a conventional timer 25.

The lamp 18, which may be of tungsten halogen, mercury vapor, short-arc xenon, or metal halide type is mounted in a lamp socket 28. The reflector 19 is of elliptical shape and surrounds the lamp 18 to reflect light generated from the lamp 18 into the optical filter element 20. The optical filter element 20 is located at the proximal end of the fiber optic light guide 21.

Figure 3A:
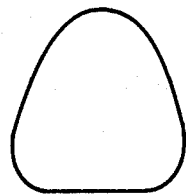
FIGS. 3A–3C are examples of end view shapes of the optic light guide of the light transmitting device of FIG. 1 tailored to correspond to the shape of different tooth surfaces.
Figure 3B:
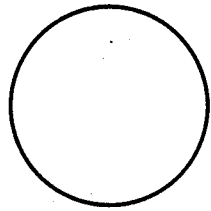
Figure 3C:
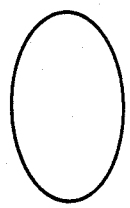

The light guide 21 is a glass, quartz or plastic fiber optic rod of any preferred length. Generally it will be no more than 3 or 4 inches long with a contoured tip 26 at the distal end thereof. The tip 26 may have any desired circular shape preferably conforming to the surface geometry of the tooth being treated. By tailoring the cross sectional geometry of the tip 26 to conform to the geometry of the tooth surface being treated little radiant energy will be lost and adjacent soft and hard tissue surfaces will not be heated or damaged. FIGS. 3A-3C show three preferred surface geometries in cross section for the tip 26 representing an ovoid, circular and modified semi-elliptical geometry respectively. The light guide 20 is held in the nose cone 30 of the housing 16 by a bushing 32 with its proximal end 34 contiguous to the optical filter element 20.

Figure 4:
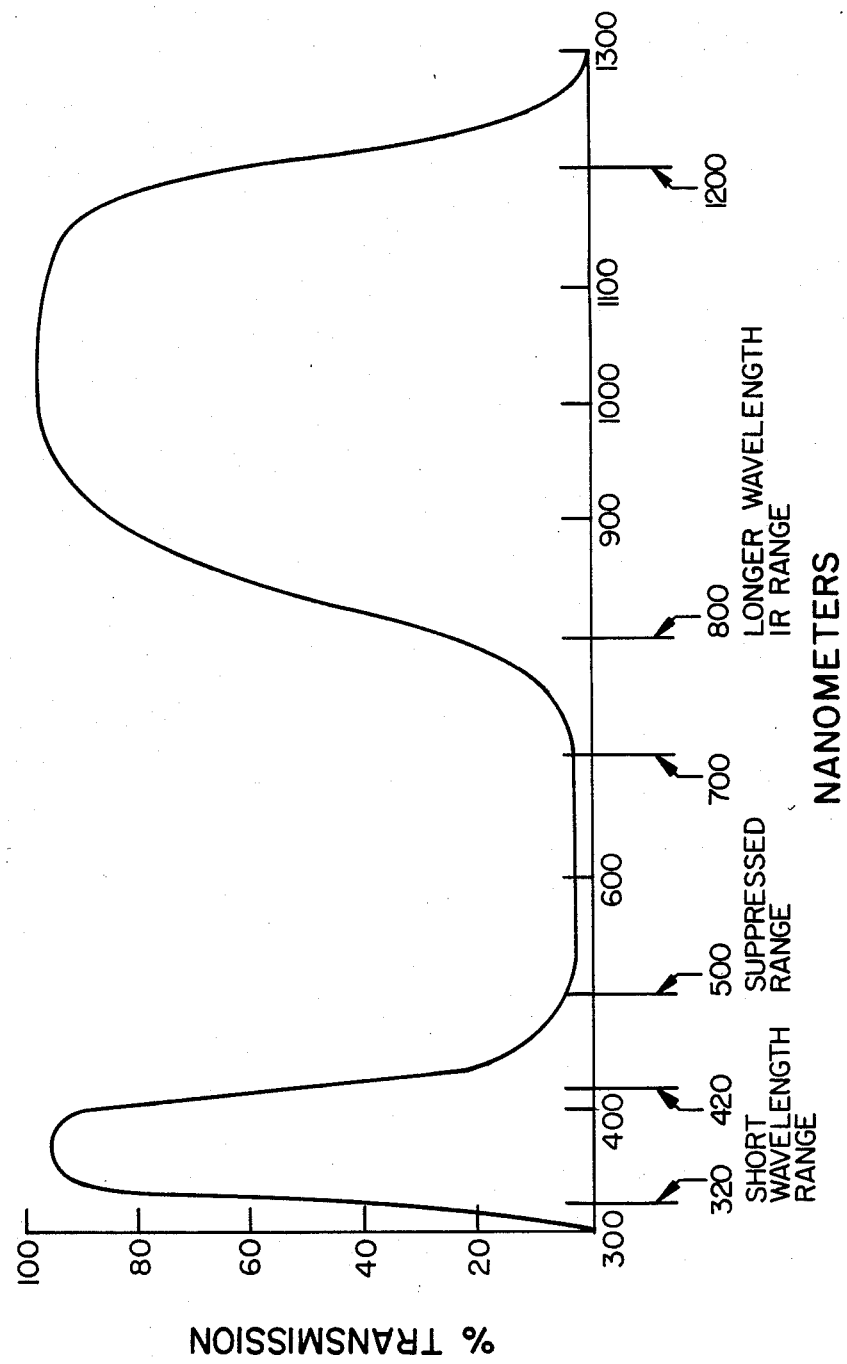
FIG. 4 is the spectral distribution curve of the optical energy transmitted through the optic light guide of the light transmitting device of FIG. 1.

The ellipsoidal reflector 19 should preferably have a dichroic coating to provide a complementary matching characteristic with that of the filter element 20. The filter element is designed as a band pass filter to block energy in the visible spectrum preferably between 500 and 700 nanometers and to pass ultraviolet energy in the region of between 320 and 420 nanometers and infrared energy in the region of between 800 to 1200 nanometers. The band pass filter element 20 can be either of a coated dichroic reflector type or of the absorption type or some combination of both. The balance of energy between ultraviolet, visible, and infrared wavelengths are controlled by selection of the characteristics of the filter. The filter spectral distribution curve for the band pass filter 20 is shown in FIG. 4.

The optical energy in the 320 to 420 nanometer range provides enhanced bleaching due to the short wavelength higher energy content in the spectrum. Long wave ultraviolet is acceptable from a safety perspective relative to energy below 300 nanometers. The 700 to 1200 nanometer region produces heat due to the longer wavelength energy. This heat penetrates the outer tooth surface and also activates the peroxide. The combined effect of the short wavelength energy and long wavelength energy improves the speed of the chemical action to increase the bleaching performance. The 500 to 700 nanometer region is suppressed and blocked. It has been found in accordance with the present invention that the energy in this latter region provides little benefit to the bleaching operation and otherwise produces visible glare which is uncomfortable for the operator.

What I claim is:

1. A method for treating discolored teeth comprising the steps of:
   applying a concentrated solution of peroxide to the pulp chamber of non-vital teeth and/or upon the surface of discolored teeth within the mouth of a dental patient;
   focusing a beam of optical energy directly upon each discolored tooth to be treated, with said beam containing ultraviolet energy in the 320 to 420 nanometer range in combination with infrared energy in the 700 to 1200 nanometer range for activating said peroxide solution; and
   substantially suppressing optical energy in the 500 to 700 nanometer range from reaching the teeth under treatment.

2. A method as defined in claim 1 wherein said beam of optical energy is generated from a light transmitting source of radiant energy through an optic light guide adapted to be held in close proximity to the tooth under treatment.

3. A method as defined in claim 2 wherein said light guide is held between 1-3 mm from the tooth under treatment.

4. A method as defined in claim 2 wherein said radiant source of light is a lamp selected from the group consisting of tungsten halogen, mercury vapor, short-arc xenon or metal halide.

5. A method as defined in claim 4 wherein said energy in the 500 to 700 nanometer range is suppressed by means of a band pass filter selected with a spectral distribution curve which attenuates energy in the aforementioned range.

6. A method as defined in claim 5 wherein said light guide is contoured at the distal end thereof to conform to the surface geometry of the tooth under treatment.

* * * * *